United States Patent [19]
Kuerzinger et al.

[11] Patent Number: 4,767,601
[45] Date of Patent: Aug. 30, 1988

[54] APPARATUS FOR THE MONITORING AND REGULATION OF MATERIAL CONCENTRATIONS IN CHEMICAL PROCESSES (I)

[75] Inventors: Karl Kuerzinger, Hanau; Peter Wachendoerfer, Frankfurt, both of Fed. Rep. of Germany

[73] Assignee: Degussa Aktiengesellshaft, Frankfurt, Fed. Rep. of Germany

[21] Appl. No.: 897,945

[22] Filed: Aug. 19, 1986

[30] Foreign Application Priority Data

Sep. 21, 1985 [DE] Fed. Rep. of Germany ....... 8527071

[51] Int. Cl.$^4$ ...................... G01N 27/00; G01N 25/20
[52] U.S. Cl. ......................................... 422/68; 422/51; 422/83; 422/95; 436/147; 436/160; 73/25
[58] Field of Search ....................... 422/51, 83, 95, 68; 436/147, 160; 73/25

[56] References Cited

U.S. PATENT DOCUMENTS

| | | | |
|---|---|---|---|
| 3,440,013 | 4/1969 | Carr et al. ............................ | 422/51 |
| 3,488,155 | 1/1970 | Ayers ................................... | 436/147 |
| 3,531,255 | 9/1970 | Fenske et al. ........................ | 436/160 |
| 3,726,644 | 4/1973 | Desnoyers et al. ................. | 436/147 |
| 4,344,917 | 8/1982 | Schorno ............................... | 422/83 |
| 4,407,963 | 10/1983 | Sørensen .............................. | 73/25 |
| 4,518,566 | 5/1985 | Sørensen .............................. | 436/147 |
| 4,555,491 | 11/1985 | Spurlin et al. ...................... | 436/120 |
| 4,592,896 | 6/1986 | Runnells et al. .................... | 422/95 |

Primary Examiner—David L. Lacey
Assistant Examiner—Lori-Ann Johnson
Attorney, Agent, or Firm—Beveridge, De Grandi & Weilacher

[57] ABSTRACT

To regulate and monitor material concentrations, e.g., sodium chlorite or hydrogen peroxide, measuring cells are used in which these substances react to completion with another substance, e.g, sulfur dioxide, in an exothermal reaction. The resulting temperature rise is then a measure of the concentration. A measuring cell comprises a pipe section provided at both ends with mounting devices for installation in the delivery line transporting the reaction medium. Within this pipe section there is positioned axially a smaller diameter pipe section which is open at both ends, into one open end of which projects the supply line for the reacting substance and at the other end of which a temperature sensor is installed.

8 Claims, 1 Drawing Sheet

APPARATUS FOR THE MONITORING AND REGULATION OF MATERIAL CONCENTRATIONS IN CHEMICAL PROCESSES (I)

The invention relates to an apparatus for the monitoring and regulation of material concentrations in chemical processes, said substances reacting to completion in an exothermal reaction with other substances, by measuring the temperature rise in said reaction. The apparatus comprises a measuring cell with supply lines for the reaction medium and the reacting substance, a discharge line, and temperature sensors. The apparatus is particularly useful for determining and monitoring hydrogen peroxide and chlorite concentration in scrubbing solutions for scrubbing the flue gases of, for example, waste incineration plants or large capacity furnace systems.

In many continuous and discontinuous chemical processes which operate with substances such as hydrogen peroxide, sodium chlorite or other oxidizing and reducing agents, it is necessary to monitor the concentration of these substances by continuously measuring and, if necessary, adjusting said concentration. This is particularly true of modern processes of flue gas scrubbing, in which sulfur dioxide is removed from the flue gases by means of scrubbing solutions containing hydrogen peroxide; or processes where nitrogen oxides are removed from flue gases by means of solutions containing sodium chlorite. Such solutions are also used, for example, for disinfecting the water in swimming pools.

Aqueous sodium chlorite solutions have recently been used to convert the nitrogen monoxide contained in the flue gases of waste incineration plants to nitrogen dioxide by wet scrubbing. In acidic chlorite solutions, more or less free chlorine dioxide, which is extremely explosive, is formed depending on the pH. Thus, it is important to monitor and adjust the chlorite concentration in such solutions in a continuous manner.

West German Pat. No. 34 37 624 discloses an apparatus by means of which hydrogen peroxide concentrations in liquid reaction media can be monitored and adjusted by reacting to completion in a measuring cell a partial stream of the hydrogen peroxide containing solution with sulfur dioxide and measuring the temperature rise resulting from the heat of reaction. The temperature rise is a measure of the heat production and thus also a measure of the hydrogen peroxide concentration in the reaction medium. Similarly, the concentrations in aqueous solutions of other oxidizing agents, such as sodium chlorite, can also be measured with sulfur dioxide or other reducing agents. The apparatus consists of a thermally insulated measuring cell, which at one end possesses a separate supply line for a partial stream of the oxidizing reaction medium and a separate supply line for the reacting substance, e.g., sulfur dioxide and, at the other end, has a discharge line. Temperature sensors for measuring the inlet and outlet temperatures of the liquids are installed at the supply lines and at the discharge line.

This measuring cell must be connected to a partial stream line of the reaction medium, and therefore this system also requires supply lines, metering apparatus, valves and/or pumps. A direct connection to the delivery line of the reaction medium is therefore desirable which, for example, would deliver the scrubbing liquid from the bottom sump to the scrubber head of an absorption column.

Accordingly, the primary object of the present invention is therefore to provide an apparatus for determining and monitoring substance concentrations in liquid media, said substances reacting to completion in an exothermal reaction with other substances, by measuring the temperature rise in this reaction, said apparatus comprising a measuring cell with supply lines for the reaction medium and the reacting substance, a discharge line, and temperature sensors, and which can be operated without additional lines and delivery components. A further object of the invention is to dispense with the thermal insulation of the measuring cell.

According to the invention, this primary object is attained by providing an apparatus comprising a pipe section with approximately the same diameter at both ends as the delivery line transporting the reaction medium, and with mounting devices for installation in the delivery line; and further, that there is axially positioned in said pipe section a smaller diameter pipe section which is open at both ends, into one open end of which projects the supply line for the reacting substance, and at the other end of which is mounted a temperature sensor for measuring the temperature rise of the mixture.

Preferably, the diameter of the inner pipe section is at most half as large as the diameter of the outer pipe section. This ensures that only a small partial stream of the reaction medium flows through the inner pipe section, which serves as the measuring cell.

The apparatus of the invention can be mounted without difficulty into a delivery line transporting the reaction medium. It does not require any additional lines, valves or pumps in order to produce a partial stream of reaction medium necessary for the measurement.

The mounting devices can be designed, for example, with a flange or a screw connection. Thermal insulation can be dispensed with, since the inner pipe section, representing the actual measuring cell, is adequately protected against external temperature influences by the reaction medium flowing in the annular clearance between the inner and outer pipe sections.

The invention is further described with reference to the drawings wherein.

Figures 1, 2:
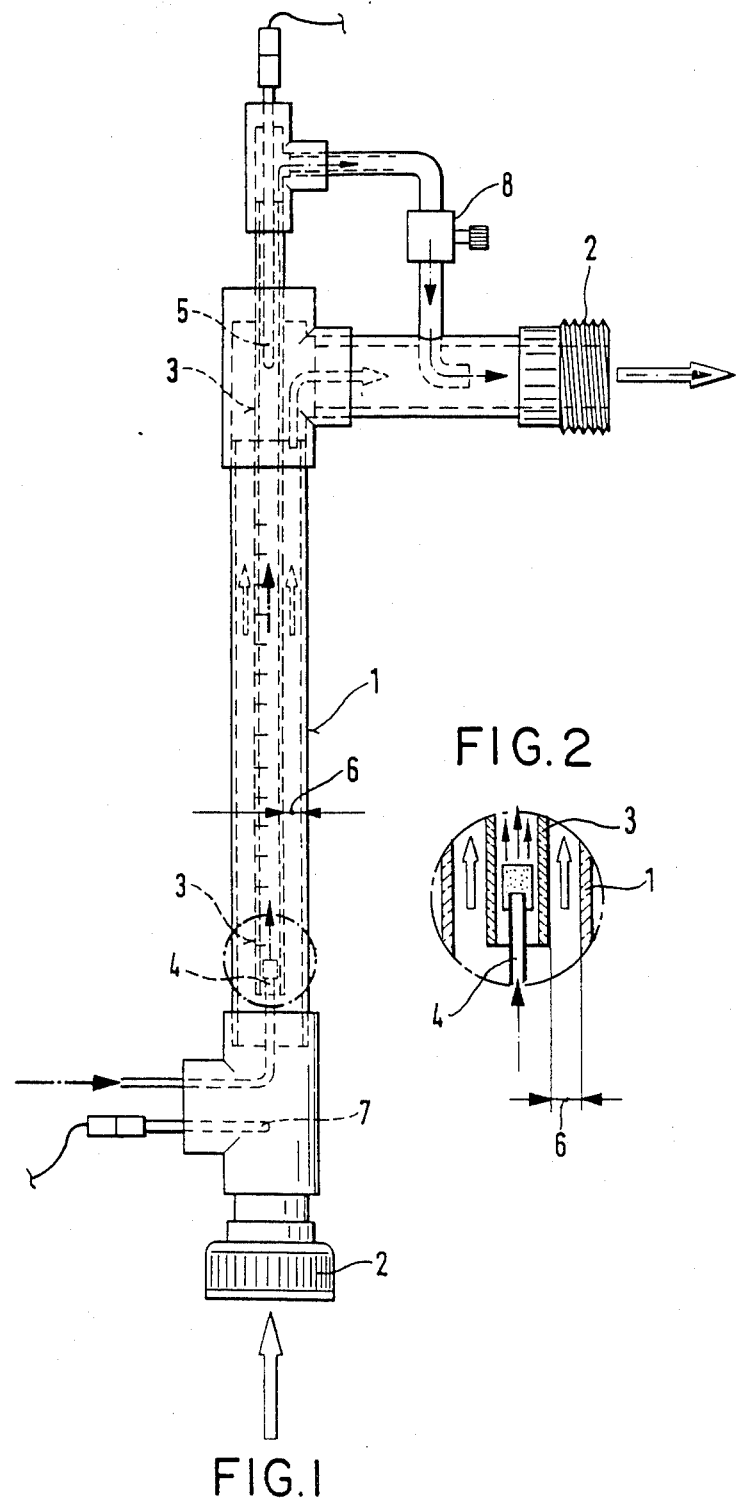
FIG. 1 shows the apparatus of the invention.
FIG. 2 is an enlargement of a section of the apparatus of the invention.

Described in further detail, FIG. 1 schematically illustrates a practical embodiment of the apparatus of the invention. This comprises a pipe section (1), the diameter of which corresponds approximately to that of mounting devices (2) at both ends of the pipe section. In pipe section (1) there is axially positioned a smaller diameter pipe section (3) which is open at both ends, and which either is located entirely in the outer pipe section (1) or projects partly out of it. It is a basic feature that the actual measuring cell, which is formed between the supply line (4) for the reacting substance projecting into the open end of the inner pipe section (3), and the temperature sensor (5), located at the other end of the inner pipe section (3), is surrounded by the outer pipe section (1) and, thus, is also surrounded by the reaction medium in the annular clearance (6). The temperature of the arriving reaction medium is measured by a temperature sensor (7) prior to the reaction medium's entry into the inner pipe section (3), and the temperature rise by the ongoing exothermal reaction, said temperature rise being a measure of the concentration of the substance to be determined, e.g., sodium chlorite or hydrogen peroxide by means of the temperature sensor (5) in the inner pipe section (3). The quantity of the partial stream which flows through the inner pipe section (3) can additionally be adjusted by means of a valve (8). Preferably, gaseous sulfur dioxide is used as the reacting substance, which is fed via the supply line (4) to the inner pipe section (3).

A detailed view of the smaller diameter pipe is shown in FIG. 2.

Further variations and modifications of the invention will be apparent to those skilled in the art from a study of the foregoing and such variations and modifications are intended to be encompassed by the claims appended hereto.

We claim:

1. An apparatus for monitoring and regulating reactant concentrations in a liquid reaction medium, said reactant reacting to completion in an exothermal reaction with a reacting substance, the apparatus being capable of measuring the temperature rise in said exothermal reaction, said apparatus comprising a measuring cell adapted for connection with a supply line for the reaction medium, a supply line for the reacting substance, a discharge line and at least two temperature sensors, wherein said measuring cell comprises a pipe section for connection to, and of approximately the same diameter as, said supply line for transporting the reaction medium, said cell being provided at each of its ends with a mounting device for connection of said cell at one end to said supply line for transporting the reaction medium and connection of said cell at its other end to said discharge line, said measuring cell having axially positioned within said pipe section a smaller diameter pipe section having a first open end and a second open end, with said supply line for the reacting substance projecting into the first open end of said smaller diameter pipe section, and said smaller diameter pipe section having an internal diameter which is larger than the outer periphery of that portion of said supply line which projects into the first open end, such that the reaction medium can flow around the outer periphery of said supply line and into the first open end so as to come in contact with the reacting substance which is flowing in the same direction within said smaller diameter pipe section; wherein said at least two temperature sensors comprise a first temperature sensor one end of which extends into the second open end of said smaller diameter pipe section, said first temperature sensor being provided for measuring the temperature rise of the chemically reacting mixture of reacting substance and reaction medium flowing therein and a second temperature sensor for measuring the temperature of the reaction medium before the reaction medium comes in contact with the reacting substance.

2. The apparatus according to claim 1, wherein the diameter of the smaller diameter pipe section (3) is at most half as large as the diameter of the outer pipe section (1).

3. An apparatus according to claim 1 wherein said pipe section is a straight pipe section having the same diameter along its entire length and two ends, each of said ends being inserted into respective a T-joint, a first of said T-joints being adapted for connection to, and of approximately the same diameter as, said supply line for transporting the reaction medium, said supply line for the reacting substance being positioned so as to extend into said first T-joint and said first temperature sensor being positioned so as to extend into a second of said T-joints and into the second open end of said smaller diameter pipe section.

4. The apparatus according to claim 3, wherein the diameter of the smaller diameter pipe section (3) is at most half as large as the diameter of the outer pipe section (1).

5. An apparatus as recited in claim 3 wherein said second T-joint includes a portion which is adapted for connection to, and is of approximately the same diameter as, said discharge line.

6. An apparatus as recited in claim 5 further comprising a third T-joint in connection with the second end of said smaller diameter pipe section, said third T-joint having said temperature sensor passing therethrough; and a portion of said smaller diameter pipe section near its second end extending through a cylindrical portion of said second T-joint which is the portion that is free from contact with said discharge line.

7. An apparatus as recited in claim 6 further comprising a Z-shaped pipe conduit having one of its ends in attachment with said third T-joint and a second of its ends in attachment with said second T-joint whereby the mixture in said smaller diameter pipe section is directed through said third T-joint and into the portion of the second T-joint which is connected to said discharge line.

8. An apparatus as recited in claim 7 further comprising valve means in connection with said Z-shaped conduit whereby adjustment of said valve results in a change in the quantity of the mixture flowing in said smaller diameter pipe section.

* * * * *